United States Patent [19]

Goble et al.

[11] Patent Number: 5,038,109

[45] Date of Patent: Aug. 6, 1991

[54] SCREENING AND MONITORING INSTRUMENT

[75] Inventors: Nigel M. Goble, Yelverton; Colin C. O. Goble, Cardiff, both of United Kingdom

[73] Assignee: Gyrus Medical Limited, Cardiff, United Kingdom

[21] Appl. No.: 417,829

[22] Filed: Oct. 6, 1989

[30] Foreign Application Priority Data

Oct. 13, 1988 [GB] United Kingdom ............... 8824001
Mar. 30, 1989 [GB] United Kingdom ............... 8907193

[51] Int. Cl.⁵ .............................................. G01N 27/02
[52] U.S. Cl. ................................... 324/439; 128/771;
324/446; 324/692; 324/724; 324/441; 324/721
[58] Field of Search ............... 324/438, 439, 441, 442,
324/446, 692, 703, 705, 724, 158 R, 721;
128/771, 734, 635

[56] References Cited

U.S. PATENT DOCUMENTS

| | | | |
|---|---|---|---|
| 3,265,962 | 8/1966 | Otto, Jr. ................................ | 324/446 |
| 4,025,307 | 5/1977 | Randolph et al. ................. | 324/71.4 X |
| 4,454,472 | 6/1984 | Moore .............................. | 324/158 R |
| 4,672,970 | 6/1987 | Uchida et al. ....................... | 128/635 |
| 4,752,740 | 6/1988 | Steininger ........................ | 324/439 X |
| 4,767,994 | 8/1988 | Hopkins et al. .................. | 324/439 X |
| 4,912,417 | 3/1990 | Gibboney et al. ................... | 324/438 |
| 4,916,075 | 4/1990 | Malmros et al. ................ | 324/71.5 X |

*Primary Examiner*—Kenneth A. Wieder
*Assistant Examiner*—Robert W. Mueller
*Attorney, Agent, or Firm*—Woodard, Emhardt, Maughton, Moriarty & McNett

[57] ABSTRACT

Apparatus for indicating a predisposition to kidney stone disease in humans, and also dehydration, and for monitoring the efficacy of hydration therapy, comprises a conductivity probe including a tip which can be inserted into urine so that a drop thereof adheres to the tip, and display means for indicating the result as a derived function of conductivity (electrolyte concentration) in terms of urine specific gravity or osmolality. Preferably the probe electrodes are small and are spaced closely together so that the streamlines between the electrode tips are such that maximum current flows substantially within the adherent drop of urine.

10 Claims, 5 Drawing Sheets

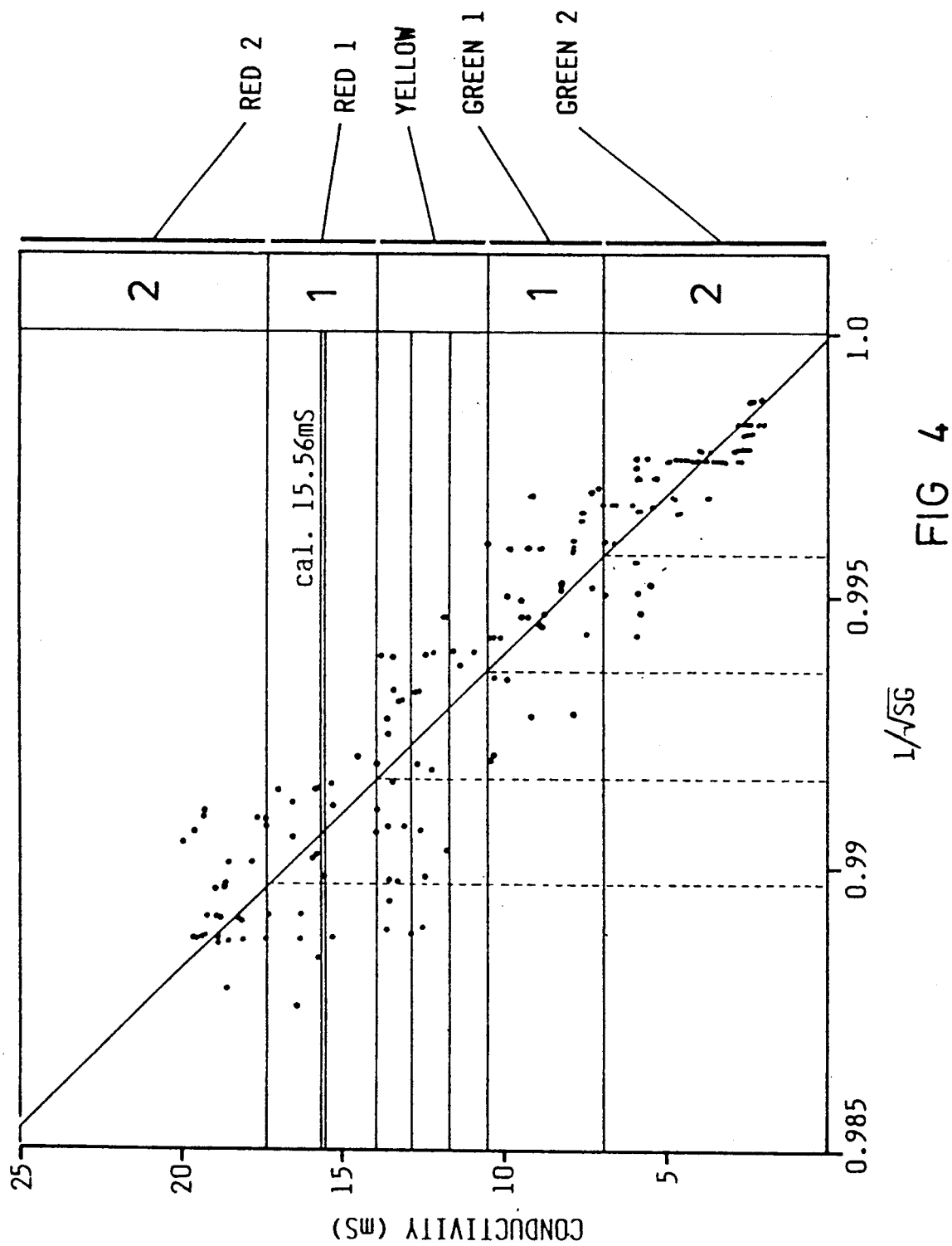

SCREENING AND MONITORING INSTRUMENT

This invention relates to the screening and monitoring of human beings to detect a predisposition to the development of kidney stone disease, to detect dehydration, or to monitor the efficacy of hydration therapy in general.

Kidney stone disease constitutes a widespread health problem among adults living in the so-called "developed countries", particularly among the relatively affluent and/or those having a sedentary or stress-related occupation. Kidney stone disease is caused by the precipitation of calcium compounds, particularly calcium oxalate, from super-saturated solutions normally stabilised against precipitation by glycoproteins. However, certain factors cause the stabilising function to break down whereby precipitation occurs with resulting deposition of solid calcium compounds which eventually accumulate to cause blockages in the kidney or elsewhere in the urinary tract. Such blockages generally cause extreme pain and discomfort and may require treatment by surgery.

It has previously been determined that, at a urine specific gravity of less than 1.015 and irrespective of any inherent tendency or otherwise to kidney stone formation, the calcium compounds are maintained in solution. At the upper limit of metastability for a given urinary sample, which for clinical purposes may be broadly represented by specific gravities greater than 1.015, a solid phase begins to develop spontaneously although dissolution may occur, at least partially, if the specific gravity falls below this limit. It follows that kidney stone disease could be avoided by drinking sufficient water to ensure that the average specific gravity of urine is maintained at or below 1.015. However, to ensure that this level is maintained requires fluid intake to be increased to a level sufficient to produce 3-4 liters of urine per day distributed, as evenly as possible, over day and night. As such it is clearly impractical to increase fluid intake to this level as a general prophylactic exercise for the population as a whole. It would accordingly be useful readily to monitor the urinary concentration of those people whose metabolism or life-style put them at risk of kidney stone formation, so that those people could take appropriate remedial action and monitor the result thereof.

It would also be useful readily to detect dehydration, particularly in children suffering from gastrointestinal infections. This usefulness would also extend to any form of medical therapy in which hydration levels play an important role.

It is an object of the present invention to provide non-invasive screening apparatus and a technique for detecting a predisposition to or likelihood of development of kidney stone disease, for detecting dehydration and for monitoring the effect of remedial action thereon, and for monitoring the efficacy of hydration therapy in general.

According to the invention, apparatus for indicating a predisposition to kidney stone disease or dehydration comprises probe means for insertion into urine so that a sample thereof attaches to the probe, means for measurement of the concentration of electrolytes in the urine sample, and display means for indicating the result.

The invention is based on the realisation that an effectively linear correlation exists, at least over the range of interest, between urine electrolyte concentration as measured by specific electrical conductivity, specific gravity and osmolality and this enables the degree to which a person is at risk of kidney stone formation, or any other pathophysiological process which relates to hydration levels, to be assessed.

Preferably, the apparatus according to the invention comprises a conductivity probe to measure the specific electrical conductivity of the urine and the urinary electrolytes comprise sodium $Na^+$, hydrogen $H^+$, ammonium $NH_4^+$ and the like.

The probe means of the inventive apparatus preferably comprises a tip including a pair of point electrodes whereby the probe tip may simply be inserted into the urine stream so that a drop of urine adheres thereto in contact with the electrodes by surface tension. With such an arrangement, it will be appreciated that the probe tip is exposed and may readily be wiped clean, unlike the arrangement with some conductivity probes wherein the electrodes are contained within a sample reservoir. An alternating current is then applied to determine the resistance, and hence the conductance, of the urine. The conductance reading will reduce with decreasing temperature, however, and it is thus preferred to include in the circuitry or operating instructions a temperature-compensation facility. The operating temperature range is generally from 15°–35° C.

One way of providing for temperature compensation is to apply electrode excitation by using two analogue switches which are alternately switched by a two-phase oscillator. The action of the analogue switches ensures that half of the current waveform appears across a thermistor compensation network mounted in close proximity to the electrodes. A voltage is therefore generated across the thermistor circuitry which is proportional to the temperature compensated electrical conductivity of the sample solution.

Another way of providing temperature compensation is to use a double-diode in a differential mode. The temperature coefficient of the diode varies with bias current. If, however, the current in each of the diodes is different, the difference in bias voltage has a positive coefficient. Unlike a negative coefficient, the positive coefficient may be used to control the reference voltage, thus negating the need for complicated amplitude control. This technique also has another advantage in that the diodes may be manufactured as a single die and are hence each subject to the same manufacturing variations. The variation in the current/voltage relationships of the individual diodes is compensated, as regards the temperature coefficient, by the fact that the overall coefficient is dependent on the ratio of the two currents rather than an absolute value. The absolute value, however, does require compensation by adjustment in the calibration procedure.

A true differential amplifier is unsuitable because of cost considerations, and moreover a truly constant current is likewise unsuitable. A compromise may be achieved by driving the higher current diode from the regulated supply, such that the higher is the forward current, the less is the coefficient and, therefore, the less the current change. In practice the current is limited by power consumption considerations. The higher current diode is thus preferably driven at approximately 300uA. The voltage in one diode provides the output with a negative coefficient, whilst the second diode confers a positive one. The positive coefficient term should be made large, and the fact that the output is a function of diode current rather than voltage for the positive coefficient, results in a non-linearity, due to the relationship $I \propto \exp[kV/T]$, where k is a constant and T is the temp. in $K^\circ$. However, over the operating temerature range of the apparatus according to the invention, the relationship is essentially linear, producing a maximum error of ±1.25%.

Preferably the electrodes are positioned close to one another, typically at a spacing of less than 2 mm, preferably no more than approximately 1 mm, and are no more than approximately 0.5 mm in width, preferably approximately 0.25 mm. With such dimensions, for example a spacing of 1 mm, an electrode width of 0.25 mm and a probe diameter of between 5 and 10 mm, it has been found that the streamlines between the electrode tips, which are cut at 90° by lines of equipotential which radiate into the sample fluid from the probe, are such that maximum current flows at or in proximity to the fluid/probe interface and hence substantially within the adherent drop of urine, the volume of which is determined by the cross-sectional area of the probe.

The electrodes are preferably made from an inert material such as platinum, in wire form, embedded in a non-conductive solid material such that the ends of the wires are exposed. Furthermore, the diameter of the wires may be minimised thereby aiding miniaturisation of the instrument and lowering the specific conductance of the cell.

Preferably the excitation frequency is as high as possible commensurate with the limitation of power consumption. The high frequency overcomes the capacitive decay that otherwise occurs using a small electrode surface area. In practice, a minimum frequency of 100KHz is desirable.

The determination of a linear correlation between urinary specific electrical conductivity and specific gravity enables the instrument to be calibrated using a test solution of known specific electrical conductivity. The instrument is then ready for use by a person to detect when the urine is more concentrated, for example after sleep at night, for assessing indirectly, under conditions likely to produce a positive result, whether that person's urine has a specific gravity in excess of 1.015. If a positive result is indicated, it will then be possible for the user to undergo a programme of fluid intake and to assess, on a continuing basis, the efficacy of such programme.

Instruments according to the invention include a suitable power source, or the means to be connected to one, electronic circuitry and a readout or other display which may simply be an indication that a particular threshold value has been attained or, alternatively, may provide more detail as to the extent to which the result is above or below the threshold.

The power source is preferably a miniature 12 v cell such as that having the I.E.C. designation VR22. The capacity of such cells is only 33mAhr but this is acceptable because of the speed of measurement, each reading requiring the instrument to be switched on for appproximately 10 seconds only. Preferably, a pure alternating current is used, since direct currents even as low as 1uA are sufficient to cause electrolysis in the urine sample and hence to cause errors. To eliminate the possibility of direct current components, the electrodes may be coupled via a coupling capacitor.

The voltage requirement for the display means may typically be 7±±0.25 v. To regulate at this level with maximum utilisation of battery capacity requires a regulator with low drop-out and low quiescent current.

The low drop-out requirement indicates the preferred use of a collector controlled supply. Collector controlled supplies are however inherently unstable and require significant damping, which may achieved by the use of two capacitors.

The supply voltage is an important factor, a requirement engendered in part by the desirability of optimising battery utilisation. The supply reference preferably therefore comprises a zener biased from the regulated supply. Bias current to the zener is maintained at a low level, preferably just over 1mA. Using such a low bias level results in an increase in the tolerance of the zener to ±2.5%. The regulated voltage is determined by a bridge configuration, in which the zener is on one side and a resistor divider on the other. The error voltage of the bridge may be detected by the full open-loop gain of an op-amp, which is a quadrant of the measurement circuitry so that it is necessarily driven from the regulated supply. The readout may be constituted by a bargraph display, preferably a "dot-mode" bargraph display. This minimises current consumption and assists a straightforward interpretation of the result. For use in indicating a predisposition to kidney stone disease, the elements of the display are related to the normal range of urinary electrical conductivity subdivided to indicate whether the user is above or below the upper limit of metastability. The bargraph may comprise five LED's driven by four level detectors, each level being one quadrant of an op-amp/comparator. Thus one LED will be illuminated irrespective of the status of the level detectors. To drive the bargraph display, an applied voltage proportional to the specific electrical conductivity is preferred. For other purposes, the readout could be dedicated to particular therapeutic applications related to hydration therapy, and could for example be arranged to give a direct reading in terms of osmolality, conductivity, or specific gravity.

Apparatus according to the invention should preferably be waterproof. Conveniently, the apparatus includes a housing which may be a unitary injection moulding, including a battery compartment which may be sealed by a screw plug which also provides the negative terminal connection. The apparatus may have power control exercised by an integrally-formed membrane switch. The overall size and shape are conveniently such that the apparatus may be carried in the pocket.

The invention also includes a method for either detecting or monitoring the treatment of dehydration, the method comprising determining the conductivity of a urine sample and obtaining therefrom a derived value relating to specific gravity or osmolality. The method also has utility for detecting or monitoring a predisposition to stone formation.

Embodiments of the invention will now be described by way of example with reference to the accompanying drawings, of which:

FIG. 4 illustrates the bargraph display and performance characteristics of a urine conductivity meter according to the invention;

Figure 5A:
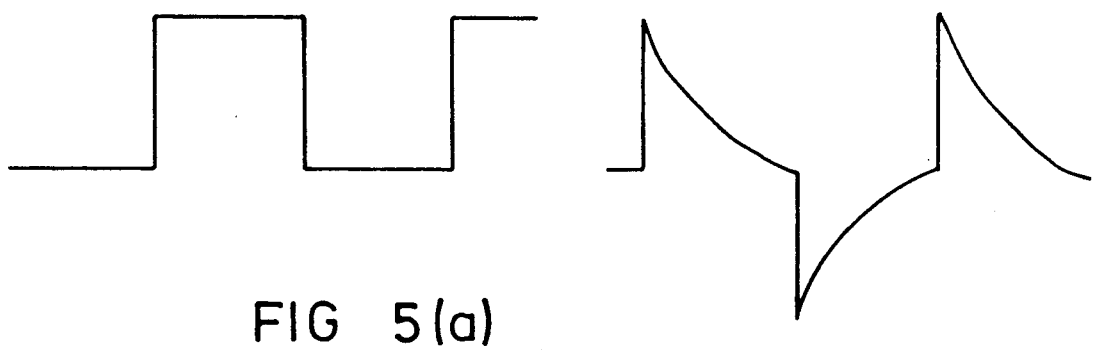
Figure 5B:
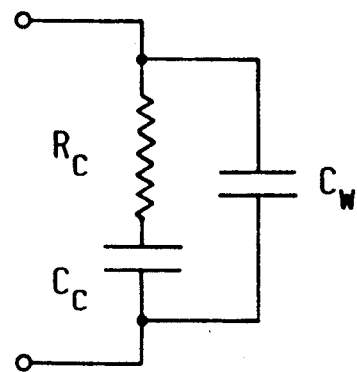
Figure 5C:
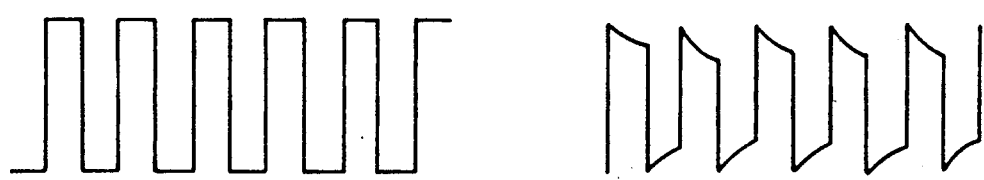

FIG. 5(a) to (c) illustrate the oscillator frequency considerations; and

Figure 6:
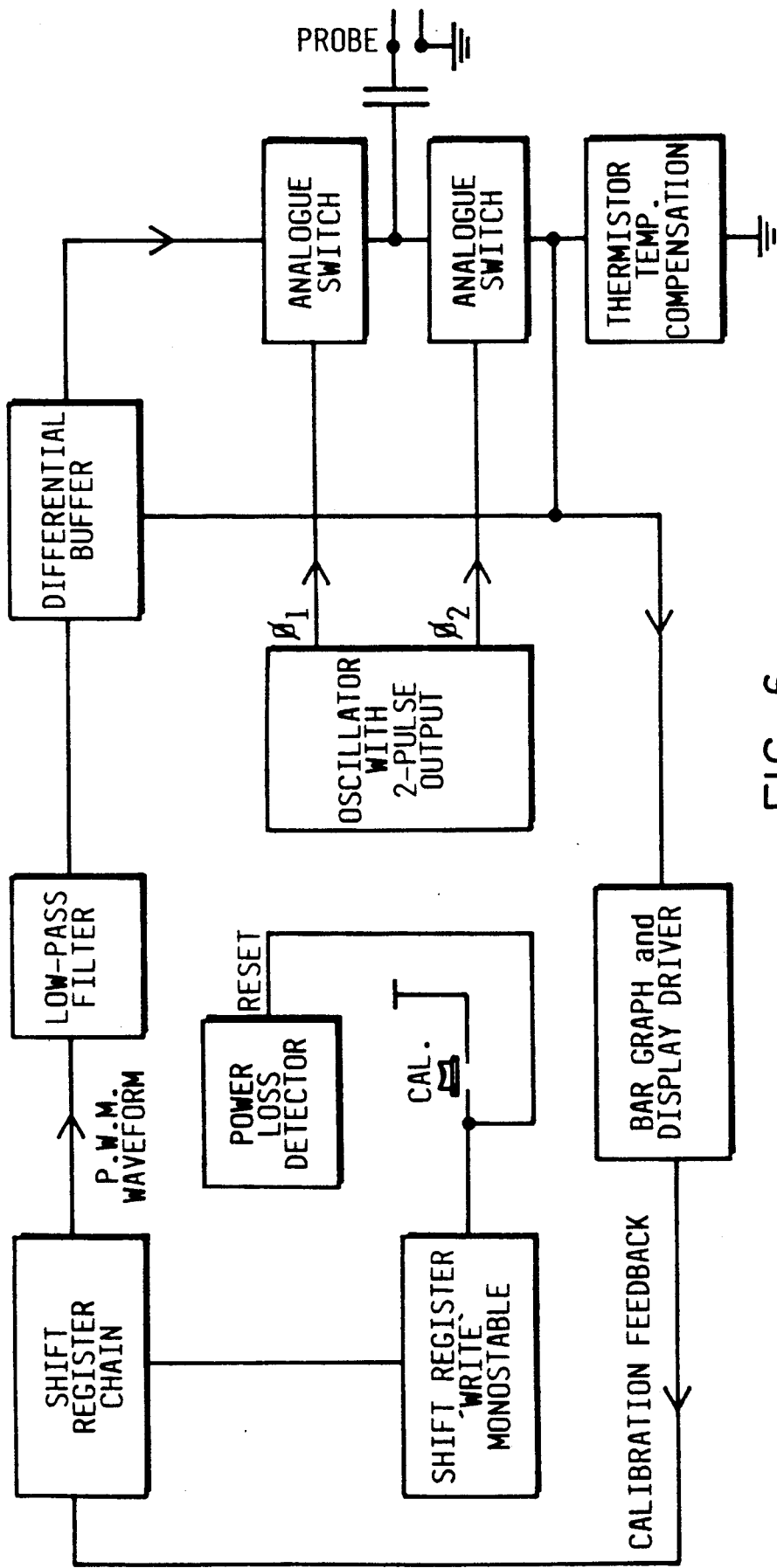

FIG. 6 shows an embodiment incorporating an auto-calibration technique.

Figure 1:
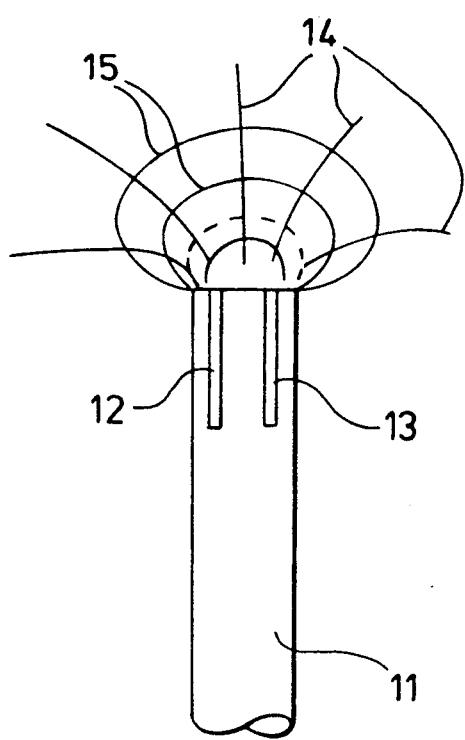
FIG. 1 shows one form of inventive probe tip.
Figure 2:
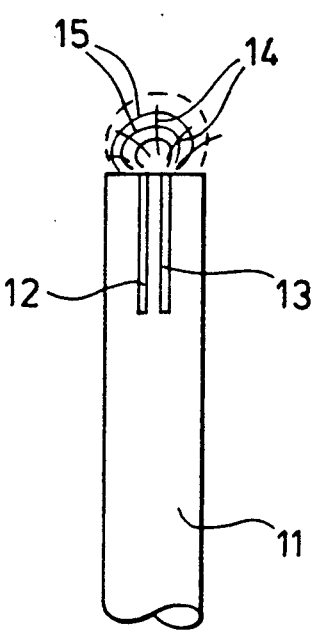
FIG. 2 shows a similar tip with reduced size and spacing of the electrodes.

With reference to FIGS. 1 and 2, a probe consists of a tip portion 11 and electrodes 12, 13. Lines of equipotential 14 radiate from the tip and the streamlines are indicated 15. The periphery of an adherent drop of urine is indicated by a dotted line.

As shown in FIG. 2, where the electrodes are approximately 0.25 mm wide with a spacing of approximately 1 mm, the streamlines are contained within the drip volume.

Figure 3:
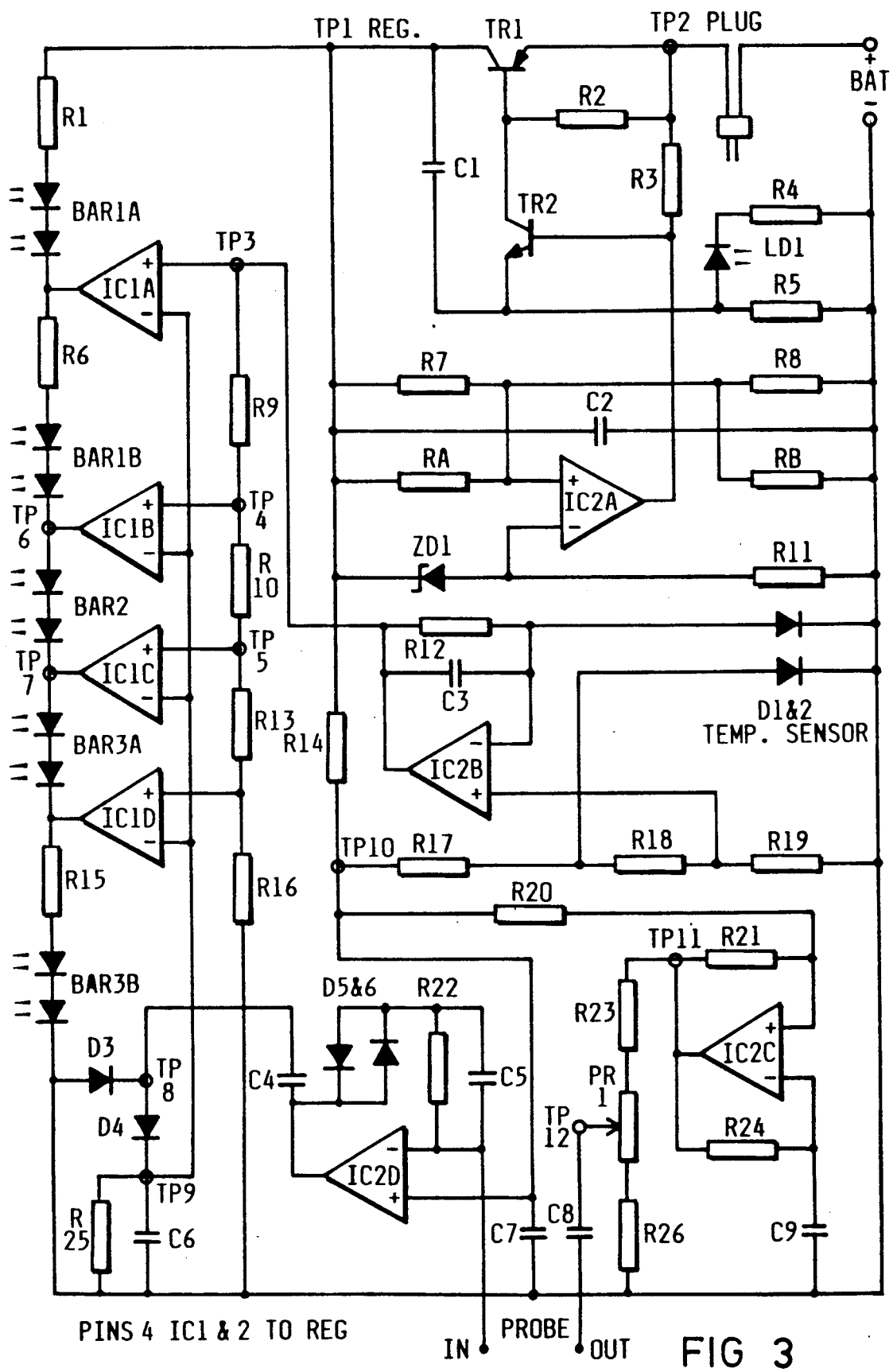
FIG. 3 shows a circuit diagram.

Referring to FIG. 3, the power source is a miniature 12 v cell, I.E.C. designation VR22. Capacitors C1 and C2 are for damping the collector-controlled supply the reference for which is a 2% zener ZD1. The bridge configuration is constituted by ZD1/R11 and R7/R8. This measures the regulated voltage whose error voltage is detected by the full open-loop gain of an op-amp (IC2A). This op-amp is a quadrant of the measurement circuitry so that it is necessarily driven from the regulated supply. The regulator is, therefore, driven from the regulated side and would not operate unless initiated from the unregulated side. The start-up of the regulator is performed by a resistor (R3) which back-drives the op-amp (IC2A) to a level sufficient to turn on TR2. This strategy relies on the output of the 'off' amplifier appearing as a reverse bias junction. All current supplied via the start resistor (R5) initially flows into the base of TR2. As the collector curcuit of TR2 begins to sink current, a threshold is reached at about 130µA where TR1 begins turns on and begins to supply the regulated side. IC2A begins to operate at voltages of about 2v. When the regulator has reached the correct voltage (7v), TR1 carries a current of 15 to 18mA. The required base current of TR1 is approximately 60µA. To both speed up the regulating circuit and null the effects of gain variations in TR1, a resistor (R2) is connected across the base emitter of TR1, thereby requiring a further 150µA to reach the forward bias voltage of TR1. Thus the collector of TR2 supplies a nominal current of approximately 200µ. The emitter of TR2 is connected, via a resistor (R5), to ground. The emitter voltage is thus elevated, for the given current, to a level of 1 v (R5=4k7). Due to current demands in the rest of the circuit, however, this voltage does have a significant ripple. Provided that there is surplus battery capacity, this voltage will not exceed 1.2 v. Connected across the emitter resistor (R5) is a LED (LD1) and a limit resistor (R4). LD1 is a low current device requiring a minimum voltage of 1.8 v before illuminating. A voltage of 1.8 v at the emitter of TR2 provides excessive base current in TR1; TR1 is thus saturated. This condition will only occur when the error voltage is high, coinciding with the point where battery voltage has fallen to a level insufficient to drive the regulator. As a consequence, the op-amp saturates at the regulated supply level. TR2 follows this voltage so that the emitter is at approximately 5.4 v. With LD1 now fully on, with a forward voltage of approximately 2 v with a current of 4mA, it indicates a low battery condition.

With regard to regulator stability, C1 provides frequency compensation for the discrete components of the regulator. By using a capacitor in the C1 position, it is possible to decouple the regulator by means of a small capacitor of 0.1µf (C2). The residual high frequency ripple in the regulated supply can, however, still cause indistinct thresholds in the bargraph display. Furthermore, the use of such a small decoupling capacitor reduces usable battery capacity due to the residual high current ripple. For this reason it is preferred to use a tantalum capacitor at C2 which, at a value of at least 10µf, obviates the need for high frequency compensation and renders C1 redundant.

The bargraph display is divided into five segments representing (i) a conductivity of <7.00mS (equivalent to a urinary specific gravity of <1.0083; (ii) conductivity 7.0-10.5mS (SG 1.0083-1.0127); (iii) conductivity 10.5-14.00mS (SG 1.0127-1.0173); (iv) conductivity 14.0-17.13mS (SG1.0173-1.0213); and conductivity >17 (SG>1.0213). These segments for convenience were coloured and known as (i) green 2; (ii) green 1; (iii)yelow; (iv)red 1 and (v) red 2. The segments are illustrated in FIG. 4 which also shows performance characteristics of 197 samples by regression analysis, the results being presented in terms of conductivity against 1/N SG, in which the conductivity fell in the range 0-20mS at R=−0.94, where R is the average correlation coefficient between specific gravity and specific electrical conductivity. In terms of osmolality, the results were similar, the correlation factor being approximately 0.95 for adults.

In FIG. 4, the central band is representative of the range of specific electrical conductivity readings which indicate a urine specific gravity of 1.015 with a confidence interval of 99.9% based on a general population. During calibration or checking, a test solution having a specific electrical conductivity of 15.56 mS should give a reading in the centre of the "Red 1" display; this will indicate that the apparatus will be correctly calibrated for use over the range of interest.

Referring to FIG. 5, the oscillator operates at a high frequency (5(c)) to overcome the capacitive decay that otherwise occurs at the electrodes at low frequencies (5(a)), in which the right-hand trace indicates the effect of capacitive delay on the output current waveform, compared with the undecayed waveform (left-hand trace). This distortion in the output current waveform is due to the capacitive effect of dissociation occurring at the electrode/solution interface. This effect may be described electrically by the circuit shown in 5(b), where $R_c$ is the non-reactive impedance of the solution, $C_c$ is the capacitance effect observed in the current waveform, and $C_w$ is the capacitance of the wires connecting to the electrodes.

The conductance of the solution is a measure of $R_c$. Therefore, the values of $C_w$ amd $C_c$ must be minimised. However, increasing the excitation frequency to try and eliminate $C_c$ results in offset errors due to $C_w$. Alternatively, $C_c$ may be minimised by increasing the surface area of the electrodes. In order to use small electrode surface areas, $C_w$ must be made as small as possible to allow increased excitation frequency without significant offset errors and, hence, to eliminate the effect of capacitive decay. 5(c) shows the effect of increasing frequency on the output current waveform, whereby only partial decay of the waveform now occurs.

Referring to FIG. 6, the excitation voltage level is preferably controlled by the integrated, pulse-width modulated waveform stored in a shift register. The stored waveform and, therefore, the excitation voltage level may then be varied using a calibration procedure. This procedure will automatically reset the range of the display according to the specific electrical conductivity of a test solution.

The normal mode for the shift register is in recycle so that the bit pattern stored in the register is recycled in an endless loop. To input a new pattern during the calibration procedure, this loop has to be broken. If this loop is broken for any length of time, the system does not have time to respond with a change of state, thus the register becomes filled with either logic 1's or 0's. The new data is thus written in to the register one bit at a time, with sufficient interval between the 'write windows' to allow the system to respond. These 'write windows' are created by a monostable which is activated by a calibration button once the probe is immersed in the test solution.

The calibration value is then stored as a pulse-width modulation waveform in the shift register. This is permanently powered by the battery so as to maintain the calibration value.

Power loss, as may occur when changing the battery, will result in loss of the stored value. Power loss is therefore detected and normal operation inhibited until the device is recalibrated. Inhibition is displayed, for example by illumination of a red segment of the display.

What is claimed is:

1. Apparatus for indicating a predisposition to kidney stone disease or dehydration, the apparatus comprising a power source, probe means for insertion into urine so that a sample thereof attaches to the said probe means, means for measurement of the concentration of electrolytes in the urine sample, and display means for indicating the result as a derived function of said concentration.

2. Apparatus according to claim 1, wherein the measurement means comprises a conductivity probe.

3. Apparatus according to claim 1, and comprising a conductivity probe, wherein the probe means comprises a tip which includes a pair of electrodes, whereby in use a drop of urine adheres to the tip in contact with the electrodes by surface tension and an alternating current may be applied to determine the resistance, and hence the conductance, of the urine, the derived function relating to specific gravity or osmolality.

4. Apparatus according to claim 3, including a temperature-compensation facility.

5. Apparatus according to claim 3 or claim 4, wherein the electrodes are spaced less than 2 mm apart and are 0.5 mm or less in width.

6. Apparatus according to claim 3 or claim 4 having electrodes spaced less than 2 mm apart and 0.5 mm or less in width, wherein the probe has a diameter between 5 and 10 mm.

7. Apparatus according to any of claim 2, wherein the probe has a minimum excitation frequency of 100 KHz.

8. Apparatus according to claim 1, wherein the display means comprises a bargraph display.

9. Apparatus according to claim 8, wherein the bargraph display is related to the normal range of urinary electrical conductivity subdivided into elements to indicate whether the specific gravity of the urine sample is above or below the upper limit of metastability.

10. A method for the detection of a predisposition to stone formation or other pathophysiological process which relates to hydration levels in humans, or for detecting or monitoring the treatment of dehydration, or for monitoring the efficacy of hydration therapy in humans, the method comprising determining the concentration of electrolytes in a urine sample from the human body and obtaining therefrom a derived function of said concentration in terms of urine specific gravity or osmolality.

* * * * *

UNITED STATES PATENT AND TRADEMARK OFFICE
CERTIFICATE OF CORRECTION

PATENT NO. : 5,038,109
DATED : August 6, 1991
INVENTOR(S) : Nigel Mark Goble et al.

It is certified that error appears in the above-identified patent and that said Letters Patent is hereby corrected as shown below:

In column 3, line 68, delete "7±±0.25 v" and insert in lieu thereof --7±-0.25v--.

In column 5, line 41, delete "200µ" and insert in lieu thereof --200µA--.

In column 6, line 14, delete "(iii}yelow" and insert in lieu thereof --(iii) yelow--; and in the same line, delete "(iv}red" and insert in lieu thereof --(iv) red--.

In column 6, line 18, delete "1/N SG" and insert in lieu thereof --1/√SG--.

Signed and Sealed this

Fifteenth Day of December, 1992

*Attest:*

DOUGLAS B. COMER

*Attesting Officer*      *Acting Commissioner of Patents and Trademarks*